United States Patent [19]

Kvakovszky et al.

[11] Patent Number: 5,304,690

[45] Date of Patent: Apr. 19, 1994

[54] PROCESS FOR THE PREPARATION OF SALTS OF 4-HYDROXYSTYRENE

[75] Inventors: George Kvakovszky; James H. Rea; Michael I. Sheehan, all of Corpus Christi, Tex.; Brad L. Smith, Matthews, N.C.

[73] Assignee: Hoechst Celanese Corporation, Sommerville, N.J.

[21] Appl. No.: 80,897

[22] Filed: Jun. 22, 1993

Related U.S. Application Data

[60] Division of Ser. No. 940,424, Sep. 3, 1992, Pat. No. 5,256,809, which is a continuation-in-part of Ser. No. 614,766, Nov. 16, 1990, Pat. No. 5,241,098.

[51] Int. Cl.$^5$ .................. C07C 39/20; C07C 69/96
[52] U.S. Cl. .................. 568/780; 558/270; 568/716
[58] Field of Search .............. 568/780, 804, 270, 716; 430/176; 558/270

[56] References Cited

U.S. PATENT DOCUMENTS

| | | | |
|---|---|---|---|
| 4,491,628 | 1/1985 | Ito et al. | 430/176 |
| 5,082,965 | 1/1992 | Nader et al. | 558/270 |
| 5,087,772 | 2/1992 | Sheehan et al. | 568/804 |
| 5,241,098 | 8/1993 | Kvakovszky et al. | 558/270 |
| 5,256,809 | 10/1993 | Kvakovszky et al. | 558/270 |

*Primary Examiner*—Werren B. Lone
*Attorney, Agent, or Firm*—James J. Mullen; Donald R. Cassady

[57] ABSTRACT

4-Acetoxystyrene is reacted with a base in a solvent to form a salt of 4-hydroxystyrene via saponification. Alternatively, 4-hydroxystyrene is reacted with a base to form a salt of 4-hydroxystyrene. In the latter case, the 4-hydroxystyrene is prepared by the transesterification of 4-acetoxystyrene. Subsequently or simultaneously, the salt of 4-hydroxystyrene is reacted, preferably in situ, with di-tertiary-butyl-dicarbonate to form 4-tertiarybutoxycarbonyloxystyrene.

14 Claims, No Drawings

PROCESS FOR THE PREPARATION OF SALTS OF 4-HYDROXYSTYRENE

RELATED APPLICATIONS

This application is a division of U.S. patent application Ser. No. 07/940,424, filed Sep. 3, 1992, U.S. Pat. No. 5,256,809, which is a continuation-in-part application of copending U.S. patent application Ser. No. 07/614,766, filed on Nov. 16, 1990, now U.S. Pat. No. 5,241,098.

TECHNICAL FIELD OF THE INVENTION

The present invention relates to salts of 4-hydroxystyrene and 4-tertiary-butoxycarbonyloxystyrene and, more particularly, to methods for the preparation thereof. Still more particularly, the present invention discloses the preparation of a salt of 4-hydroxystyrene from 4-acetoxystyrene and the preparation of 4-tertiarybutoxycarbonyloxystyrene from said salt.

BACKGROUND OF THE INVENTION

The compound 4-hydroxystyrene is a well-known compound which is useful as a food flavoring substance and as an intermediate in the preparation of polymers and copolymers utilized in the manufacture of coatings, electronic components, ion exchange resins, photoresists, etc. Although there are several known methods of preparing 4-hydroxystyrene, those methods are not commercially feasible in the further utilization of 4-hydroxystyrene, such as, for example, for use in the preparation of a photoresist intermediate such as 4-tertiarybutoxycarbonyloxystyrene. The reason for this is that the 4-hydroxystyrene is difficult to 4-solate because it readily polymerizes and decomposes and is toxic via &kin absorption. A preparation for 4-hydroxystyrene utilizing 4-acetoxystyrene is reported in a paper entitled "Preparation of Vinylphenols and Isopropenylphenols", Corson et al., Volume 23, April 1958 *J. Org. Chem.* In that preparation, 4-acetoxystyrene is saponified in an aqueous system with a large concentration of a soluble base, KOH, to produce an aqueous solution of the potassium salt of 4-hydroxystyrene which is neutralized with acid to precipitate 4-hydroxystyrene. The procedure is not practical or commercially feasible for production of large quantities of 4-hydroxystyrene because the 4-hydroxystyrene is not stable and readily polymerizes under the aqueous saponification conditions employed therein which involve high concentrations of soluble base. A more efficient process for producing 4-hydroxystyrene from 4-acetoxystyrene is desired and needed. The present invention provides a method wherein excessive polymerization of the 4-acetoxystyrene and/or the 4-hydroxystyrene in the formation of 4-hydroxystyrene is avoided.

The compound 4-tertiary-butoxycarbonyloxystyrene is useful as an intermediate in the production of the photoresist material poly(4-tertiary-butoxycarbonyloxystyrene). A route to 4-tertiarybutoxycarbonyloxystyrene is reported by Frechet et al., Polymer, 1983, 995 and Ito et al., U.S. Pat. No. 4,491,628, which involves a Wittig reaction starting with p-hydroxybenzaldehyde.

U.S. Pat. No. 5,082,965 also discloses a process for the preparation of alkoxycarbonyloxystyrene. Acyloxystyrene is reacted with a strong base in an aqueous medium to yield a phenolate. An alkoxycarbonylating agent is then added in an organic solvent and a phase transfer catalyst to yield the desired product.

The formation of 4-tertiarybutoxycarbonyloxystyren directly from p-hydroxystyrene has never been publicly reported, most likely due to the fact of the great instability of the 4-hydroxystyrene, as discussed above, and the difficulties most likely encountered thereby. These difficulties would lead one skilled in the art away from trying such synthesis using 4-hydroxystyrene even in the face of the synthesis of 4-tertiary-butoxycarbonyloxy-α-methylstyrene from 4-hydroxy-α-methylstyrene, as reported in U.S. Pat. No. 4,491,628. The reason for this is that α-methylstyrenes are much more stable to polymerization than unsubstituted styrenes such as 4-hydroxystyrene.

These and other objects and advantages of the present invention will become apparent from the following description.

SUMMARY OF THE INVENTION

According to the present invention a relatively stable salt of 4-hydroxystyrene is prepared directly from 4-acetoxystyrene by the saponification or hydrolysis of 4-acetoxystyrene. 4-Acetoxystyrene is reacted with an ionic organic base such as a metal alkoxide or an inorganic base such as a metal hydroxide in an organic solvent in which the 4-acetoxystyrene is readily soluble and the metal alkoxide or the metal hydroxide is either marginally soluble or readily soluble or in water. The salt of 4-hydroxystyrene so formed is then reacted, simultaneously or subsequently, in situ with 4-di-tertiary-butyldicarbonate to form 4-tertiary-butoxycarbonyloxystyrene.

Furthermore, according to the present invention the salt of 4-hydroxystyrene is prepared by reacting 4-hydroxystyrene with an ionic organic base such as metal alkoxide or an inorganic base such as a metal hydroxide. The salt of 4-hydroxystyrene is reacted, simultaneously or subsequently, in situ with di-tertiary-butyldicarbonate to form 4-tertiary-butoxycarbonyloxystyrene. The 4-hydroxystyrene used for the preparation of the salt thereof is preferably prepared by the transesterification of 4-acetoxystyrene.

The salt of 4-hydroxystyrene prepared according to the present invention can be neutralized to form 4-hydroxystyrene which, following concentration by cold filtration and freeze-drying under vacuum must be stored at low temperature. The 4-hydroxystyrene so formed can be used later in many applications.

DETAILED DESCRIPTION OF THE INVENTION

According to the present invention, a salt of 4-hydroxystyrene of the formula

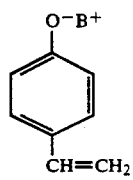

(hereinafter referred to as "Salt of 4-hydroxystyrene") is prepared directly from 4-acetoxystyrene of the formula

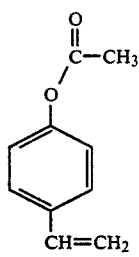

(hereinafter referred to as "4-Acetoxystyrene") by the saponification or hydrolysis of 4-acetoxystyrene. B is the cationic moiety of a Base BX which is defined below. 4-Acetoxystyrene is a known compound which can be synthesized in accordance with the teachings of Corson et al., *J. Org. Chem.* 23, 544 (1958). 4-Acetoxystyrene is reacted with a base of the formula BX (hereinafter referred to as "Base BX" wherein B is the cationic moiety and X is the anionic moiety of the base to form the Salt of 4-Hydroxystyrene. The reaction is carried out in an organic solvent in which Base BX is either "readily soluble" or "marginally soluble" and in which the 4-Acetoxystyrene is "readily soluble" or in water. As the term "readily soluble" is used herein, a Base BX is "readily soluble" in a solvent when the solubility of the Base BX in the solvent is sufficiently high so that substantially all of the Base BX that is present in the reaction mass is dissolved in the solvent whereby the reaction is substantially a one phase, i.e. a liquid phase, reaction. As the term "marginally soluble" is used herein, a Base BX is marginally soluble in a solvent when the solubility of the Base BX in the solvent is low so that only a small amount of the Base BX that is present in the reaction mass is dissolved in the solvent with the remaining being in the solid phase whereby the reaction is a two phase reaction.

Bases that can be used as Base BX in the above reaction are those which can hydrolyze or saponify the 4-Acetoxystyrene to form the Salt of 4-Hydroxystyrene directly. Such bases include alkali metal alkoxides (ionic organic bases) such as $NaOCH_3$, $KOC(CH_3)_3$, etc.; and inorganic bases such as metal hydroxides, preferably alkali metal hydroxides, such as KOH, NAOH, LIOH, etc., more preferably KOH and NAOH, and, most preferably KOH. one or a mixture of two or more of the above bases may be used. It is preferred that, when a metal hydroxide base is used as Base BX, the amount thereof being available in the reaction mass to react with the 4-Acetoxystyrene be regulated so that the metal hydroxide base is only available to react with the 4-Acetoxystyrene but unavailable to promote polymerization reactions. This is accomplished by utilizing a solvent wherein the metal hydroxide base which is used as Base BX is marginally soluble whereby a small amount of the metal hydroxide base which is present in the reaction mass dissolves in the solvent and is available to react with the 4-Acetoxystyrene while the remaining metal hydroxide base is in the solid phase. As the reaction progresses and dissolved metal hydroxide base is consumed, additional small amount of base is dissolved to replace the consumed base.

In an alternative method according to the present invention, the Salt of 4-Hydroxystyrene is also prepared by reacting 4-hydroxystyrene with an equivalent amount or concentration of a Base BX (as defined above). The 4-hydroxystyrene is prepared by any well known method such as the method disclosed in U.S. patent application Ser. No. 07/614,767 by Michael T. Sheehan et al., entitled "A METHOD FOR PREPARING 4-HYDROXYSTYRENE", filed on Nov. 16, 1990, now U.S. Pat. No. 5,087,772 (hereinafter referred to as the "Sheehan Methods"). In the Sheehan Method, the 4-hydroxystyrene is prepared by the transesterification of 4-Acetoxystyrene. That application is incorporated herein and made part hereof by reference in its entirety.

Furthermore, according to the present invention, the Salt of 4-Hydroxystyrene which may be prepared as described above, is reacted with di-tertiary-butyldicarbonate of the formula

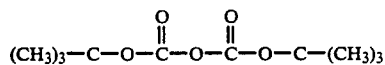

(hereinafter referred to as "IDBDC") to form 4-tertiarybutoxycarbonyloxystyrene of the formula

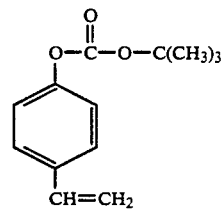

(hereinafter referred to as "t-Boc-Styrene") The reaction for the preparation of t-Boc-Styrene is preferably carried out in situ subsequently to or simultaneously with the preparation of the Salt of 4-Hydroxystyrene described above. More particularly, the reaction of the Salt of 4-Hydroxystyrene with DBDC is carried out without isolating the Salt of 4-Hydroxystyrene from the reaction medium.

The preferred embodiments which follow further describe the invention.

(a) Preparation of the Salt of 4-Hydroxystyrene by Reacting 4-Acetoxystyrene with a Metal Hydroxide Base in an Organic Solvent in Which the Metal Hydroxide Base is Marginally Soluble and Preparation of t-Boc-Styrene.

In the first embodiment, the 4-Acetoxystyrene is reacted with a metal hydroxide base which serves as Base BX in a suitable solvent system to form the Salt of 4-Hydroxy styrene. A suitable solvent system is a solvent system comprising at least one suitable solvent. A suitable solvent is one in which the 4-Acetoxystyrene is soluble and the metal hydroxide base which serves as Base BX is only marginally soluble so that a two-phase reaction system is formed. In that reaction system, homo- and copolymerization of 4-Hydroxystyrene, Salt of 4-Hydroxystyrene and 4-Acetoxystyrene (which occurs when the metal hydroxide base is present in quantities exceeding those consumed in its reaction with the 4-Acetoxystyrene) is avoided. An example of this type of reaction system is one when the solvent is ethyl acetate and the metal hydroxide base is potassium hydroxide. The suitable solvent selected is, of course, dependent upon the metal hydroxide selected and the Salt of 4-Hydroxystyrene resulting therefrom which has to be soluble in such solvent. For the most common metal hydroxides, e.g. sodium and potassium hydroxide, etc., some suitable solvents in which the Salt of 4-

Hydroxystyrene is soluble are ethyl acetate, methyl acetate, butyl acetate, toluene, and tetrahydrofuran.

The metal hydroxide can be mixed directly with the suitable solvent or can be dissolved in a second solvent which may or may not be miscible with the suitable solvent, provided that a suitable two-phase reaction system results. The metal hydroxide which serves as Base BX is reacted with the 4-Acetoxystyrene in amounts sufficient to fully saponify the 4-Acetoxystyrene. Typically, the stoichiometric amount of two (2) moles of metal hydroxide per mole of 4-Acetoxystyrene is used.

The 4-Acetoxystyrene is typically reacted with the metal hydroxide at a temperature of from about −20° C. to about 125° C., at a pressure ranging from about 1.0 to about 10.0 atmospheres and for a time period ranging from about 30 minutes to about 8.0 hours.

It has surprisingly been found that, unlike conventional saponification of 4-Acetoxystyrene in a miscible aqueous solvent system, the two-phase reaction system of the instant invention leads to good yields of the Salt of 4-Hydroxystyrene without an inordinate amount of polymerization of 4-Acetoxystyrene, 4-hydroxystyrene or Salt of 4-Hydroxystyrene. Accordingly, it is critical that the reaction be conducted under reaction conditions whereby the concentration of the metal hydroxide base is kept low during reaction. This can be accomplished by the resultant two-phase system described.

The resultant Salt of 4-Hydroxystyrene may be neutralized, such as for example by the addition of acetic acid to form, essentially polymer free, 4-Hydroxystyrene which may then be concentrated by cold filtration and freeze-dried under vacuum. This isolated 4-Hydroxystyrene should be stored below 0° C. due to its thermal instability above this temperature.

The Salt of 4-Hydroxystyrene can be used in the preparation of t-Boc-Styrene which is useful as a starting material in the preparation of polymers for use in photoresists. Heretofore, there has been no published method of producing t-Boc-Styrene directly from 4-hydroxystyrene, due to the unstable nature of 4-hydroxystyrene, the ease of polymerization thereof, the fact that it easily decomposes, and the fact that it is very hygroscopic and very difficult to dry.

It has now been discovered that t-Boc-Styrene can be synthesized from the Salt of 4-Hydroxystyrene which has been formed as described above, by reacting the Salt of 4-Hydroxystyrene so formed in situ to form t-Boc-Styrene. The Salt of 4-Hydroxystyrene is formed, as described above, by the reaction of 4-Acetoxystyrene with the metal hydroxide base which serves as Base BX, e.g. KOH, in the presence of the suitable solvent, e.g. ethylacetate, at a suitable temperature, e.g. 30° C. The Salt of 4-Hydroxystyrene, in turn, is reacted in situ with DBDC to form t-Boc-Styrene. Typically this reaction is conducted at a temperature of about 0° to 40° C. for about 0.5 to about 4.0 hours.

Surprisingly, it has been found that t-Boc-Styrene produced in situ from the Salt of 4-Hydroxystyrene, as described above, is readily formed in good yields without evidence of large polymerization or decomposition products resulting from either 4-Acetoxystyrene or the Salt of 4-Hydroxystyrene. It is hypothesized that this result occurs because the synthesis of the Salt of 4-Hydroxystyrene occurs directly under conditions which avoid high concentrations of the metal hydroxide base.

(b) Preparation of the Salt of 4-Hydroxystyrene by Reacting 4-Acetoxystyrene with an Equimolar Amount of a Metal Hydroxide Base in an Organic Solvent in Which the Metal Hydroxide Base is Readily Soluble and Preparation of t-Boc-Styrene.

In the second embodiment, the Salt of 4-Hydroxystyrene is prepared by reacting the 4-Acetoxystyrene with an equimolar amount of a metal hydroxide which serves as Base BX in a solvent in which the metal hydroxide, the 4-Acetoxystyrene and the Salt of 4-Hydroxystyrene are readily soluble. Examples of such solvents include organic alcohols such as methanol. An example of a reaction system of this embodiment is one wherein the solvent is methanol and the metal hydroxide is potassium hydroxide.

Contrary to the reaction which was discussed in the previous embodiment wherein the amount of the metal hydroxide base was controlled so that the metal hydroxide base was only available to react with the 4-Acetoxystyrene and unavailable to react to promote polymerization reactions, a molar amount of metal hydroxide is dissolved in the solvent. As a result, although a substantial amount of the Salt of 4-Hydroxystyrene is formed, polymers of the 4-Acetoxystyrene and the Salt of 4-Hydroxystyrene are also formed.

In carrying out the reaction, an amount of metal hydroxide required to convert substantially all of the 4-Acetoxystyrene, typically two (2) moles of metal hydroxide per mole of 4-Acetoxystyrene, is dissolved in the solvent. The solution is charged to a reactor which contains a solution of 4-Acetoxystyrene in the same solvent and the reaction is carried out over a relatively short period of time, typically about thirty (30) minutes to about one (1.0) hour.

In this reaction system, because the metal hydroxide is dissolved in the solvent, a molar amount of metal hydroxide is available not only to react with the 4-Acetoxystyrene but also to cause the polymerization of 4-Acetoxystyrene and the Salt of 4-Hydroxystyrene. In order to reduce the polymerization of those compounds, the reaction is carried out at a reduced temperature in the range of about −20° C. to about 25° C. and, preferably, in the range of about −10° C. to about 10° C. Furthermore, the reaction is carried out for a relatively short period of time in the range of about thirty (30) minutes to about one (1.0) hour under atmospheric pressure.

The resultant Salt of 4-Hydroxystyrene can be neutralized to form 4-Hydroxystyrene which may be concentrated, freeze-dried and stored, as described in the previous embodiment. Furthermore, the Salt of 4-Hydroxystyrene can be reacted in situ with DBDC to form t-Boc-Styrene. The reaction is carried out at a temperature in the range of about 0° C. to about 40° C. for about 0.5 hours to about 4.0 hours.

(c) Preparation of the Salt of 4-Hydroxystyrene by Reacting 4-Acetoxystyrene with a Metal Alkoxide Base in an Organic Solvent in which the Metal Alkoxide Base is Marginally Soluble and Preparation of t-Boc-Styrene.

In the third embodiment, the 4-Acetoxystyrene is reacted with an ionic organic base such as an alkali metal alkoxide which serves as Base BX in a suitable solvent system to form the Salt of 4-Hydroxystyrene. A suitable solvent system is a solvent system comprising at least one suitable solvent. A suitable solvent is one in which the 4-acetoxystyrene is readily soluble and the ionic organic base such as alkali metal alkoxide, which serves as Base BX, is only marginally soluble so that a two phase reaction system is formed. An example of this type of reaction system is when the solvent is hexane and the metal alkoxide base is potassium methoxide. The suitable solvent selected is dependent upon the ionic organic base selected and the Salt of 4-Hydroxystyrene resulting therefrom which has to be soluble in such solvent. For the most common alkali metal alkoxides, such as sodium and potassium methoxide and potassium t-butoxide, suitable solvents for this reaction system are non-polar organic compounds such as hexane and heptane.

The ionic organic base can be mixed directly with the suitable solvent or it can be dissolved in a second solvent which may or may not be miscible with the suitable solvent, provided that a suitable two phase reaction system results. The ionic organic base which serves as Base BX is reacted with the 4-Acetoxystyrene in amounts sufficient to fully saponify the 4-Acetoxystyrene. Typically, in a case in which an alkali metal alkoxide is used as Base BX, one mole of alkali metal alkoxide is required per mole of 4-Acetoxystyrene to fully saponify the 4-Acetoxystyrene. In addition to the Salt of 4-Hydroxystyrene, an alkyl acetate is formed which is an ionic organic compound.

The 4-Acetoxystyrene is typically reacted with the ionic organic base, such as alkali metal alkoxide, at a temperature of from about $-20°$ C. to about $25°$ C., at a pressure ranging from about 1.0 to about 10.0 atmospheres and for a time period ranging from about 30 minutes to about 8.0 hours.

The resultant Salt of 4-Hydroxystyrene can be neutralized to form 4-Hydroxystyrene which may be concentrated, freeze-dried and stored, as described as in the previous embodiment. Furthermore, the Salt of 4-Hydroxystyrene can be reacted in situ with DBDC to form t-Boc-Styrene in a reaction which is carried out at a temperature in the range of about $0°$ C. to about $40°$ C. for about 0.5 hours to about 4.0 hours.

(d) Preparation of the Salt of 4-Hydroxystyrene by Reacting 4-Acetoxystyrene with an Equimolar Amount of Metal Alkoxide Base in which the Metal Alkoxide Base is Readily Soluble and Preparation of t-Boc-Styrene.

In the fourth embodiment of this invention, the Salt of 4-Hydroxystyrene is prepared by reacting 4-Acetoxystyrene with an alkali metal alkoxide which serves as Base BX. Examples of such alkoxides include NaOCH$_3$ and KOC(CH$_3$)$_3$.

The reaction is carried out by reacting the 4-Acetoxystyrene with an equivalent amount of an ionic organic base such as an alkali metal alkoxide in a solvent in which the ionic organic base such as the alkali metal alkoxide, 4-Acetoxystyrene and the Salt of 4-Hydroxystyrene are readily soluble. Surprisingly, the yield of the Salt of 4-Hydroxystyrene is good without an inordinate amount of polymerization.

In carrying out the reaction, an equivalent amount of one (1) mole of alkali metal alkoxide per mole of 4-Acetoxystyrene is used to fully saponify the 4-Acetoxystyrene. The reaction is carried out at a temperature in the range of about $-20°$ C. to about $25°$ C. and, preferably, in the range of about $-10°$ C. to about $10°$ C. at atmospheric pressure and a time period in the range of about 30 minutes to about one (1.0) hour.

Like in the previous embodiments, the resultant Salt of 4-Hydroxystyrene can be neutralized to form 4-Hydroxystyrene which may be concentrated, freeze-dried and stored, as previously described. Furthermore, like in the previous embodiments, the Salt of 4-Hydroxystyrene can be reacted in situ with DBDC to form t-Boc-Styrene. The reaction is carried out at a temperature in the range of about $0°$ C. to about $40°$ C. for about 0.5 hours to about four (4.0) hours.

(e) Preparation of the Salt of 4-Hydroxystyrene from 4-Hydroxystyrene and Preparation of t-Boc-Styrene.

In the fifth embodiment for the formation of t-Boc-Styrene, 4-Acetoxystyrene is made by using 4-hydroxystyrene synthesized by the Sheehan Method. The 4-hydroxystyrene is then reacted with a base to form the Salt of 4-Hydroxystyrene. In the Sheehan Method, the 4-Acetoxystyrene is reacted, via a transesterification, with a suitable alcohol in the presence of a catalytic amount of a base to form 4-hydroxystyrene. The 4-hydroxystyrene is subsequently reacted with a base according to the present invention, to produce the Salt of 4-Hydroxystyrene. The Salt of 4-Hydroxystyrene is then converted to t-Boc-Styrene as described above by reacting it with DBDC.

When the Salt of 4-Hydroxystyrene is produced by the reaction of a base with 4-hydroxystyrene produced by the transesterification route, suitable alcohol for the transesterification reaction is an alcohol or a suitable mixture of alcohols having the formula ROH (hereinafter referred to as "Formula Ill), where R is a lower alkyl, where the term "lower" means the group it is describing contains from 1 to 6 carbon atoms; the term "alkyl" refers to a straight or branched chain hydroxycarbon containing no unsaturation, e.g. methyl, ethyl, propyl, isopropyl, butyl, 2-butyl, n-pentyl, n-hexyl, etc.

The lower the molecular weight and the less branching of the alkyl group, R, the better is the alcohol in terms of the yield of the target Salt of 4-Hydroxystyrene. Preferred alcohols of Formula I are methanol, ethanol, propanol and isopropanol and the most preferred are methanol and ethanol. It is understood that a suitable mixture of the foregoing alcohols can be employed.

A base of the kind useful in the transesterification reaction includes inorganic bases such as metal hydroxides, preferably an alkali metal hydroxide, e.g. KOH, NaOH, LIOH, etc., more preferably KOH and NAOH, and most preferably KOH; an alkali metal alkoxide such as NaOCH$_3$, KOCH$_3$, KOC(CH$_3$)$_3$, etc.; inorganic carbonates, e.g. K$_2$CO$_3$; alkali organic acid salts, such as potassium acetate, etc.; a nitrogen base such as lower trialkylamines, e.g. trimethylamine, triethylamine, tripropylamine, etc. which is readily soluble in the alcohol of Formula I. It is to be understood that a suitable mixture of the foregoing bases can be employed.

By a "catalytic amount" is meant an amount of base which will optimize the yield of the Salt of 4-Hydroxystyrene at the time and temperature selected to run the reaction, with a minimum amount of polymerization of the 4-Acetoxystyrene. This catalytic amount can readily be determined for the suitable alcohol, suitable base, time and temperature selected, by one of ordinary skill in the art without an undue amount of experimentation in the light of the disclosure contained herein. Typically, in terms of a mole percent of the suitable base to 4-Acetoxystyrene a catalytic amount of a suitable base such as KOH ranges from about 1.5 mole percent to about 3.6 mole percent.

Upon reaction of the 4-Acetoxystyrene with a suitable alcohol e.g. methanol, in the presence of the catalytic amount of the suitable base, e.g. about 0.5 to about 3.0 mole percent of KOH, 4-hydroxystyrene forms in good yields, with a minimum amount of polymerization of the 4-Acetoxystyrene. In addition, to 4-hydroxystyrene, an acetate ester of the formula

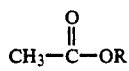

(hereinafter referred to as "Formula "II"") forms. The resultant reaction accordingly is a transesterification type reaction. Transesterification reactions typically are catalyzed with acid and usually proceed very well in the presence of acid. It has been found that attempts to react the 4-Acetoxystyrene with a suitable alcohol of Formula I, in the presence of acid, leads to polymerization of 4-hydroxystyrene and/or 4-Acetoxystyrene rather than formation of target 4-hydroxystyrene. Accordingly, the utilization of the suitable base is critical. It is also critical that only the catalytic amount of suitable base be employed. For example, if large concentrations of the suitable base, e.g. KOH, are employed, such as those concentrations typically employed in aqueous saponification, then the Salt of 4-Hydroxystyrene, is formed; a great degree of undesirable polymerization, however, occurs.

The concentration of the suitable alcohol of Formula I to 4-Acetoxystyrene during the reaction therebetween, is in excess of a 1 to 1 molar ratio, typically ranging from about 10 to about 20 times in excess of alcohol of Formula I to 4-Acetoxystyrene.

The reaction may be conducted at a temperature typically ranging from about 25° C. to reflux, for a period of time sufficient to complete the reaction. In this regard, the higher the temperature the shorter the reaction time that is necessary. In addition, the greater the catalytic amount employed at a particular temperature the less will be the reaction time. For example with about 1.5 molar percent of the suitable base, e.g. KOH, at reflux temperature e.g. 65° C. for methanol, the reaction time is typically about 4 to about 5 hours to get complete reaction of the 4-Acetoxystyrene, whereas at a catalytic amount of about 3.0 mole percent of the suitable base, e.g. KOH, at the same reflux temperature, the reaction time is typically about 1 to about 2. 5 hours to get essentially complete reaction of 4-Acetoxystyrene.

The acetate ester of Formula II, e.g. methyl acetate, may be removed during the course of the reaction to drive the reaction and the formation of 4-hydroxystyrene to completion. Additionally, resultant salt, e.g. the potassium salt form of the Salt of 4-Hydroxystyrene, present in the excess suitable alcohol is neutralized, such as for example by the addition of acetic acid, whereafter the excess alcohol of Formula I is removed from the reaction container, by any conventional manner, as for example by evaporation under reduced pressure; followed by recrystallization of 4-hydroxystyrene from a suitable solvent, such as toluene, benzene and mixtures of aromatic hydrocarbons, e.g. benzene, toluene, etc., with a paraffin, such as hexane, petroleum ether, etc., at a temperature ranging from −78° C. to 25° C. In addition, 4-hydroxystyrene can be redissolved in a suitable solvent such as an alcohol, e.g. methanol, and reprecipitated from solution by the addition of water to obtain isolated 4-hydroxystyrene.

The resultant 4-hydroxystyrene, after conversion to a salt, can be used in the preparation of t-Boc-Styrene. Due to the instability of 4-hydroxystyrene, however, is not practical to isolate this compound and use it as a starting material for t-Boc-Styrene.

It has now been discovered that t-Boc-Styrene can be synthesized from 4-hydroxystyrene by a "one-pot" or in situ reaction of 4-hydroxystyrene. The 4-hydroxystyrene is formed, as described above, by reaction of 4-Acetoxystyrene with an alcohol of Formula I in the presence of the catalytic amount of suitable base at a suitable temperature, e.g. 65° C. The resultant 4-hydroxystyrene is not isolated but is further reacted in situ with an equimolar amount or concentration of the suitable Base BX to form the Salt of 4-Hydroxystyrene, where B is the cationic moiety of the suitable base. This salt formation is typically carried out at a temperature of about −10° C. to about 25° C. for a time period sufficient to form the Salt of 4-Hydroxystyrene (typically about 10 to 20 minutes).

The Salt of 4-Hydroxystyrene, in turn, can be reacted in situ with the di-tertiary-butyl-dicarbonate to form t-Boc-Styrene. Typically this reaction is conducted at a temperature of 0° C. to 40° C. for 0.5 to 4 hours.

Surprisingly, it has been found that the Salt of 4-Hydroxystyrene is readily formed and that polymerization of 4-hydroxystyrene is minimized. It is hypothesized that this surprising result occurs because 4-hydroxystyrene is not isolated. This therefore leads to good yields, of at least 50%, (typically 70% to 85%) of the Salt of 4-Hydroxystyrene (Compound V).

(f) Simultaneous Indirect land Direct Conversion of 4-Acetoxystyrene to the Sa4t of 4-Hydroxystyrene and Conversion of the Salt of 4-Hydroxystyrene to t-Boc-Styrene.

In a sixth embodiment of the present invention, a method which is a hybrid of some of the previous preferred embodiments is used to produce, ultimately, 4-tertiary-butoxycarbonyloxystyrene. In this fifth embodiment, 4-Acetoxystyrene is again reacted with a base; however, the solvent system in which the reaction takes place is one in which solvents of the kind described as "suitable solvents" in the first preferred embodiment herein (for example, but not limited to ethylacetate, methylacetate, butylacetate, toluene, and tetrahydrofuran) are used in combination with alcohols of Formula I of the kind described in the fourth embodiment herein (for example, but not limited to, methanol, ethanol, propanol, and isopropanol). The alcohols are typically miscible with the "suitable solvents" and therefore are available to react with the 4-Acetoxystyrene, via a transesterification reaction, to produce 4-hydroxystyrene. Thus, a portion of the Salt of 4-Hydroxystyrene is produced by direct reaction of the base with 4-Acetoxystyrene, while another portion thereof is produced by transesterification of 4-Acetoxystyrene to 4-hydroxystyrene with subsequent reaction with the base to form the Salt of 4-Hydroxystyrene.

In any case, it is important that the amount of base present during the reaction process be carefully controlled so the undesired polymerization products previously described do not form. In addition, if the Salt of 4-Hydroxystyrene is immediately converted to t-Boc-Styrene this also helps avoid the formation of the polymerization products. With these considerations in mind, the reaction to convert the 4-Acetoxystyrene to the Salt of 4-Hydroxystyrene is starved for the base by adding such base continually (or in small quantities) during the reaction. In addition, the di-tertiary-butyl-dicarbonate is also typically added continually during the reaction.

There is some evidence that DBDC reacts with the base and, therefore, an excess of DBDC is used, in combination with its continual addition, to compensate for this potential side reaction.

Bases useful in this embodiment of the invention include organic bases such as metal hydroxides, preferably alkali metal hydroxides, e.g. KOH, NAOH, LIOH, etc., preferably KOH and NAOH, most preferably KOH; and alkali metal alkoxides (ionic organic base) such as NaOCH$_3$, KOC (CH$_3$)$_3$, etc. and combinations thereof. The reaction conditions used are those equivalent to the reaction conditions described in the first embodiment herein.

The yields of 4-tertiarybutoxycarbonyloxystyrene achieved range from about 80% to 98+% based on 4-Acetoxystyrene starting material.

(g) Preparation of the Salt of 4-Hydroxystyrene by Reacting 4-Acetoxystyrene with a Base in Water and Preparation of t-Boc-Styrene.

In another embodiment of the present invention, the Salt of 4-Hydroxystyrene is prepared by reacting 4-Acetoxystyrene with an equivalent amount of a metal hydroxide in water. The amount of water is sufficiently high to dissolve the 4-Acetoxystyrene, the metal hydroxide and the resultant Salt of 4-Hydroxystyrene. Although an excess amount of metal hydroxide may be used in the range of about two (2.0) moles to about 3.5 moles of metal hydroxide per mole of 4-Acetoxystyrene, it is preferred that about two (2.0) moles be used to avoid formation of polymers and consumption of DBDC in the second step which is described below. The reaction is carried out at a temperature of about 0° C. to about 25° C., under atmospheric pressure and for a time period of about 0.5 hours to about three (3.0) hours.

It should be noted that, if a metal alkoxide is added to the aqueous system above instead of the metal hydroxide to react with 4-acetoxystyrene, the metal alkoxide is converted to the corresponding metal hydroxide because of the presence of water. As a result, the reaction proceeds as discussed above.

DBDC dissolved in an inert organic solvent which is immiscible with water such as ethyl acetate, toluene, hexane, methylene chloride, etc., is added to the reaction mass. The reaction mass is thoroughly mixed at a reaction temperature in the range of about 0° C. to about 40° C. The DBDC reacts with the Salt of 4-Hydroxystyrene in a two phase aqueous/organic system to form t-Boc-Styrene.

Although it is not necessary to carry out the reaction of DBDC with the Salt of 4-Hydroxystyrene, a phase transfer catalyst may be added to the system. Examples of such catalyst include tetrabutylammonium chloride and tetrabutylammonium hydroxide.

Upon the completion of the reaction, the organic phase is separated from the aqueous phase. The t-Boc Styrene is removed from the organic layer by well known techniques such as distillation.

The following examples further illustrate the invention, but are not to be constructed as limitations on the scope of the invention contemplated herein.

EXAMPLES

Examples 1-5 are in support of the first embodiment of the invention, as previously described, wherein a relatively stable Salt of 4-Hydroxystyrene is prepared by reacting 4-Acetoxystyrene with a Base BX in a suitable solvent system in which the base is marginally soluble. The Salt of 4-Hydroxystyrene is then reacted with tertiary-butyl-dicarbonate (DBDC) to form 4-tertiary butoxycarbonyloxystyrene (t-Boc-Styrene).

Example 1

A solution of 4-acetoxystyrene (100 grams) in ethyl acetate (506 grams) was placed under one atmosphere of pressure and a nitrogen purge. Pulverized potassium hydroxide pellets (51 grams) was charged in one lot to the solution. Molten di-tertiary-butyl-dicarbonate (189 grams), was added, in small increments, over a period of 33 minutes. The contents of the vessel were stirred at 25° C., with ice-bath cooling, for an additional 2.3 hours. After aqueous wash, the organic phase (628 grams), was analyzed by gas chromatography ("GC") and was found to contain 49 grams of unchanged 4-acetoxystyrene and 32 grams (24% yield) of 4-tertiary-butoxycarbonyloxystyrene.

Example 2

A solution of 4-acetoxystyrene (101 grams) in ethyl acetate (506 grams) was placed under atmospheric pressure under a nitrogen purge. Pulverized potassium hydroxide (87 grams) was charged to the solution in one lot. The reaction was stirred at 23° C. with cooling by ice-bath for a period of about 4 hours. Then, di-tertiary-butyl-dicarbonate (191 grams) was charged over a period of 37 minutes and the reaction was stirred at 23° C. for an additional hour. After aqueous wash of the reaction product, GC analysis showed that the organic phase contained 103.5 grams (77% yield) 4-tertiarybutoxycarbonyloxystyrene.

Example 3

A solution of 4-acetoxystyrene (76 grams) in ethyl acetate (380 grams), was placed under atmospheric pressure under a nitrogen purge. Pulverized potassium hydroxide (65 grams) was added to the solution in one lot. The reaction was stirred at 12° C. with ice-bath cooling. After 2 hours, the reaction product was washed with 146 grams of water. The organic phase was separated and 133 grams molten di-tertiary-butyl-dicarbonate was added over a period of 37 minutes. After an additional 2 hours of reaction, the reaction solution was analyzed by GC and was found to contain 84.4 grams (84% yield) 4-tertiarybutoxycarbonyloxystyrene.

Example 4

To a solution of 4-acetoxystyrene (40 grams) in ethyl acetate (101 grams), was placed under atmospheric pressure and a nitrogen purge. Potassium hydroxide pellets (28 grams) were charged to the solution in one lot. A reaction was carried out for about 5 hours at 24° C. Then, molten di-tertiary-butyl-dicarbonate (62 grams), was introduced over a period of 20 minutes. After 2 hours, the thick slurry was diluted with 101 grams of ethyl acetate and stirred for an additional hour. After aqueous washing the solvent was stripped on a rotary evaporator and the residual oil was charged with 0.04 grams phenothiazine. Distillation at 0.1 mm Hg gave 45 grams (84% yield) 4- tertiary-butoxycarbonyloxystyrene.

Example 5

A solution of 4-acetoxystyrene (101 grams) in ethyl acetate (506 grams) , was placed under atmospheric pressure and nitrogen purge. Pulverized potassium hydroxide (85 grams) was added in portions, so as to maintain the reaction temperature at 40° C. After 3 hours of reaction, 191 grams of molten di-tertiary-butyl-dicarbonate was added, over a period of 37 minutes, and the reaction was stirred at 40° C. for an additional 1.3 hours. After aqueous washing of the reaction product, the organic layer was analyzed by G.C. The yield of 4-tertiarybutoxycarbonyloxystyrene (IV) was 95 grams (71% yield).

Examples 6–8 are in support of the second embodiment of the invention, as previously described, wherein the Salt of 4-Hydroxystyrene is prepared by reacting 4-acetoxystyrene with our equimolar amount of a metal hydroxide in which the metal hydroxide is readily soluble. The Salt of 4-Hydroxystyrene is then reacted with DBDC to form t-Boc-Styrene.

Example 6

Methanol (268.1 grams) and 4-acetoxystyrene (75.87 grams) were charged to the reactor and cooled to 9–10° C. A solution of 31.42 grams potassium hydroxide in 63.0 grams methanol was charged over a thirty minute period, with ice-bath cooling at 9–10° C. Immediately after complete addition of KOH/MEOH solution, 99.63 grams di-tert-butyl dicarbonate ("DBDC") was charged over a 30 minute period with ice-bath cooling to maintain the temperature at 9–10° C. After the addition of DBDC was complete, the reaction was allowed to warm to 23° C. After an additional two hours, the reaction mass was analyzed on the gas chromatograph. The yield of t-Boc-Styrene was 69.4%

Example 7

The procedure described in Example 6 was repeated by using 75.89 grams 4-Acetoxystyrene, 44.87 grams KOH and 99.67 grams DBDC instead of the corresponding amounts used in Example 6. The yield of t-Boc-Styrene was 28.8%.

Example 8

The procedure described in Example 6 was repeated by using 76.01 grams 4-Acetoxystyrene, 31.33 grams KOH and 127.57 grams DBDC instead of the corresponding amounts used in Example 6. The yield of t-Boc-Styrene was 84.64%.

Examples 9–10 are in support of the fourth embodiment of the present invention, as described above, wherein, the Salt of 4-Hydroxystyrene is prepared by reacting 4-acetoxystyrene with an equimolar amount of a metal alkoxide in a solvent in which the metal alkoxide is readily soluble. The Salt of 4-Hydroxystyrene so formed is reacted with DBDC to form t-Boc-Styrene.

Example 9

To a solution of 4-acetoxystyrene (75.84 grams) in methanol (149.93 grams) was charged, over a period of 18 minutes, a 25 wt. % solution of sodium methoxide (Aldrich) containing 25.90 grams sodium methoxide in 77.70 grams methanol. The methoxide solution was charged at 12° C. The reaction was allowed to warm to 23° C. After an additional three (3) hours the reaction was washed with 216.20 grams water and taken up in 186.40 grams hexane. The solvent was stripped and the residual oil (84.67 grams) was analyzed by GC and LC. The yield of t-Boc-Styrene was 74.76 grams (73.9%).

Example 10

To a solution of 75.56 grams 4-acetoxystyrene in 149.88 grams methanol was charged, over a period of 15 minutes, a 25 wt. % solution of sodium methoxide (Aldrich) containing 25.90 grams sodium methoxide in 77.70 grams methanol. The methoxide solution was charged at 12° C. with ice-bath cooling. Neat di-tert-butyl dicarbonate (100.40 grams) was added over a period of 30 minutes at 12° C. The reaction was allowed to warm to 23° C. After an additional hour, 429.44 grams of reaction mass was analyzed by GC. The yield of t-Boc-Styrene was 96.8 grams (95.9%).

Examples 11 and 12 are in support of the fifth embodiment of the invention, as previously described, wherein 4-hydroxystyrene is produced by the transesterification of 4-Acetoxystyrene in the presence of a catalytic amount of a base, followed by reaction of the 4-hydroxystyrene with a base to form the Salt of 4-Hydroxystyrene. The Salt of 4-Hydroxystyrene is then reacted with di-tertiary-butyl-dicarbonate to form 4-tertiary-butoxycarbonyloxystyrene.

Example 11

A solution comprising 2.4 grams of potassium hydroxide, 201 grams 4-acetoxystyrene and 500 grams of methanol was heated at reflux for 2.2 hours. The reaction was cooled to 12° C. and 64 grams potassium hydroxide pellets were added over a period of 10 minutes. After warming to 25° C., 314 grams di-tertiary-butyl-dicarbonate was introduced over a period of one hour. After an additional 2.3 hours of reaction time, the reaction slurry was washed with water and extracted with ethyl acetate. The ethyl acetate was stripped from the extraction mixture using a rotary evaporator, and the residual oil was charged with 0.26 grams phenothiazine inhibitor. Distillation at 0.1 Mm Hg yielded 227.2 grams (85% yield) 4-tertiarybutoxycarbonyloxystyrene.

Example 12

A solution comprising 0.49 grams potassium hydroxide, 40 grams of 4-acetoxystyrene, and 100 grams of absolute ethanol was refluxed for 4 hours. The reaction solution was cooled to 28° C. and 13 grams of potassium hydroxide pellets were added over a period of 10 minutes. After an additional 30 minutes of reaction, 64 grams di-tertiary-butyl-dicarbonate was charged portionwise over 20 minutes and the reaction was stirred for an additional hour at 28° C. After aqueous washing, the reaction product was extracted with ethyl acetate. The ethyl acetate was stripped from the extraction mixture on a rotary evaporator and the residual oil was charged with 0.07 grams phenothiazine. Distillation at 0.1 Mm Hg gave 34.2 grams (64%) 4-tertiary-butoxycarbonyloxystyrene.

Examples 13–15, which each include multiple experiments, are in support of the sixth embodiment of the invention which pertains to a hybrid method of forming 4-tertiary-butoxycarbonyloxystyrene.

Example 13

A solution of 85 grams (1.3 moles) of potassium hydroxide in 161 grams of methanol was added in periodic additions along with 229 grams (1.0 moles) of di-t-butyl dicarbonate to a stirred solution of 101 grams (0.65 moles) of 4-acetoxystyrene in 505 grams of ethyl acetate over a period of about 40 minutes. The reagents were added concurrently in approximately equal aliquots while the reaction mixture was kept at 25° C. with an ice bath. After an additional 2 hours of reaction at 25° C., the reaction slurry was washed well with water to remove solids. The volatile components of the organic layer were stripped under vacuum to give 148 grams (83% crude yield) of 4-tertiary-butoxycarbonyloxystyrene. Vacuum distillation afforded 87 grams (65% yield) of pure product, b.p. 111° C./0.25 mm.

Example 14

A solution of 751 grams (4.6 moles) of 4-acetoxystyrene in 3767 grams of ethyl acetate was charged to a 12-liter three-necked flask equipped with a mechanical stirrer, condenser, and ice-bath. A solution of 634 grams (0.8 moles) of potassium hydroxide in 1197 grams of methanol, and 1685 grams (7.6 moles) of molten di-tert-butyl dicarbonate was added in small portions to the stirred reaction mixture, over a period of 1 hour 20 minutes. The reaction temperature was maintained at 25° C. throughout the addition. The contents of the vessel were stirred an additional 1.4 hours at 25° C. The reaction slurry was washed twice with 4-liter portions of deionized water. The organic layer was vacuum stripped at 35° C. and 50 mm Hg until most of the solvent had been removed. The residue was further stripped at 75° C. and 1.5 Mm Hg. The residual oil, 1015 grams (99.5% conversion and 82% yield, based on 4-acetoxystyrene) was vacuum distilled to yield pure 4-tertiary-butoxycarbonyloxystyrene. Yields observed in multiple experiments employing the above procedure are shown below. The method was not yet optimized in terms of all of the variables, which variables may have differed slightly from batch to batch, accounting for the range in yield.

| Batch No. | % Yield t-Boc-Styrene |
| --- | --- |
| 1 | 86.7 |
| 2 | 90.0 |
| 3 | 90.0 |
| 4 | 97.1 |
| 5 | 81.3 |
| 7 | 90.8 |
| 8 | 92.1 |
| 9 | 96.1 |

Example 15

The reaction described in Example 14 was repeated, except that 10% less di-tert-butyl dicarbonate (6.8 moles) was used. The yields of tert-butoxycarbonyloxystyrene, 4-acetoxystyrene basis, observed in multiple runs, employing this procedure, are shown below.

| Batch No. | % Yield t-Boc-Styrene |
| --- | --- |
| 1 | 98.1 |
| 2 | 95.2 |
| 3 | 98.4 |
| 4 | 94.3 |
| 5 | 97.9 |
| 6 | 97.3 |
| 7 | 94.7 |
| 8 | 92.3 |
| 9 | 97.2 |

Examples 16–21 are in support of the last embodiment of the present invention, as described above, wherein the salt of 4-Hydroxystyrene is prepared by reacting 4-Acetoxystyrene with an equivalent amount of a metal hydroxide in water. DBDC and an inert, organic solvent which is immiscible with water and then added to the reaction mass. The DBDC reacts with the Salt of 4-Hydroxystyrene in a two phase aqueous/organic system to form t-Boc-Styrene.

Example 16

A solution of 10.4 grams potassium hydroxide in 65 grams deionized water was treated with 15 grams 4-acetoxystyrene over 10 minutes with ice-bath cooling to maintain 20–25° C. The resulting solution was treated with a mixture of 20.2 grams di-tert-butyl dicarbonate and 0.15 grams tetrabutylammonium chloride in 70 grams ethyl acetate. The reaction was mixed at 25° C. for 2.5 hours. Mixing was stopped and the upper organic layer allowed to separate from the lower aqueous layer. The organic layer was water washed and stripped on a rotary evaporator yielding 21.2 grams crude t-Boc-Styrene product (40.5%).

Example 17

A solution of 10.8 grams potassium hydroxide in 65 grams deionized water was treated with 15 grams 4-acetoxystyrene over 10 minutes with ice-bath cooling to maintain 20–28° C. The resulting solution was treated with a mixture of 20.2 grams di-tert-butyl-dicarbonate and 0.10 grams tetrabutylammonium hydroxide in 70 grams ethyl acetate. The reaction mass was mixed at 25° C. for 2. 5 hours. Mixing was stopped and the upper organic layer was allowed to separate from the lower aqueous layer. The organic layer was washed with water and stripped on a rotary evaporator yielding 22.0 grams crude t-Boc-Styrene product (34.7 %).

Example 18

A mixture of 15.03 grams 4 acetoxystyrene and 54.74 grams water was treated over a period of 30 minutes with a solution of 10.5 grams potassium hydroxide in 11.4 grams water with ice-bath cooling. The reaction was stirred at 12° C., yielding a homogeneous solution. After 2.0 hours, the reaction was treated, over a period of 30 minutes, with a solution of 20.11 grams di-tert-butyl dicarbonate (DBDC) in 70.00 grams ethyl acetate. After the addition of DBDC was complete, the reaction was allowed to warm to 23° C. and was stirred for 2.5 hours. The upper organic layer was allowed to phase separate and the solvent was stripped on the rotary evaporator. The residual oil 18.76 grams was analyzed by GC and LC. The yield of t-Boc-Styrene was 15.35 grams (76.5%).

Example 19

A mixture of 15.42 grams 4-acetoxystyrene and 54.79 grams water was treated over a period of 30 minutes with a solution of 15.99.grams potassium hydroxide in 11.5 grams water, with ice-bath cooling. The reaction was stirred at 12° C. After 15 minutes, the reaction was treated, over a period of 30 minutes, with a solution of 24.55 grams di-tert-butyl dicarbonate (DBDC) in 73.78 grams ethyl acetate. After the addition of DBDC was complete, the reaction was allowed to warm to 23° C. and was stirred for 2. 5 hours. The upper organic layer was allowed to phase separate and the solvent was stripped on the rotary evaporator. The residual oil (26.59 grams) was analyzed by GC and LC. The yield of t-Boc-Styrene was 10.49 grams (51.0%).

Example 20

A mixture of 15.87 grams 4-acetoxystyrene and 54.90 grams water was treated over a period of 30 minutes with a solution of 15.06 grams potassium hydroxide in 11.57 grams water, with ice-bath cooling. The reaction was stirred at 12° C. After 15 minutes, the reaction was treated, over a period of 30 minutes, with a solution of 24.65 grams di-tert-butyl dicarbonate (DBDC) in 72.23 grams hexane. After the addition of DBDC was complete, the reaction was allowed to warm to 23° C. and was stirred for 2.5 hours. The upper organic layer was allowed to phase separate and the solvent was stripped on the rotary evaporator. The residual oil (22.77 grams) was analyzed by GC and LC. The yield of t-Boc-Styrene was 17.33 grams (69.9%).

Example 21

A mixture of 76.03 grams 4-acetoxystyrene and 366.79 grams dichloromethane was treated, simultaneously, over a period of 15 minutes with 161.89 grams di-tert-butyl dicarbonate and a solution of 192.5 grams potassium hydroxide in 132.2 grams water, with ice-bath cooling. The reaction was stirred at 23° C. for 5 hours, followed by the addition of 400 millimeters water. The upper organic layer was washed with an additional 400 milliliters water and, after phase separation, the solvent was stripped on the rotary evaporator. The residual oil (89.4 grams) was analyzed by GC and LC. The yield of t-Boc-Styrene was 59.62 grams (48.8%).

While the invention is described with respect to specific embodiments, modification hereof can be made by one skilled in the art without departing from the spirit of the invention. The details of said embodiments are not to be construed as a limitation except to the extent indicated in the following claims.

What is claimed is:

1. A method of preparing a salt of 4-hydroxystyrene, comprising the step of reacting 4-acetoxystyrene with a base in an organic solvent.
2. The method according to claim :C wherein the base is a metal hydroxide.
3. The method according to claim 2 wherein the solvent is a solvent in which the metal hydroxide is readily soluble.
4. The method according to claim i wherein the solvent is a solvent in which the metal hydroxide is marginally soluble and the reacting step is carried out in a two phase reaction system.
5. The method according to claim -Y wherein the metal hydroxide is an alkali metal hydroxide.
6. The method according to claim 5 wherein the alkali metal hydroxide is potassium hydroxide.
7. The method according to claim 1 wherein the base is a metal alkoxide.
8. The method according to claim 7 wherein the solvent is a solvent in which the metal alkoxide is readily soluble.
9. The method according to claim 7 wherein the solvent is a solvent in which the metal alkoxide is marginally soluble and the reacting step is carried in a two phase reaction system.
10. The method according to claim 5 wherein the metal alkoxide is an alkali metal alkoxide.
11. The method according to claim 10 wherein the alkali metal alkoxide is potassium alkoxide.
12. The method according to claim 10 wherein the solvent is a solvent in which the alkali metal alkoxide is readily soluble.
13. The method according to claim 5 wherein the solvent is a solvent in which the alkali metal hydroxide is readily soluble.
14. The method according to claim 1 further including the steps of:
   forming 4-hydroxystyrene; and
   interacting the 4-hydroxystyrene with an additional base.

* * * * *

UNITED STATES PATENT AND TRADEMARK OFFICE
CERTIFICATE OF CORRECTION

PATENT NO. : 5,304,690
DATED : April 19, 1994
INVENTOR(S) : George A. Kvalkovszky, et. al.

It is certified that error appears in the above-indentified patent and that said Letters Patent is hereby corrected as shown below:

Column 18, Claim 2, line 4, delete [:C], and insert 1.

Column 18, Claim 4, line 9, delete [i], and insert 2.

Column 18, Claim 5, line 13, delete [-Y], and insert 2.

Column 18, Claim 10, line 26, delete [5], and insert 7.

Signed and Sealed this

Thirtieth Day of August, 1994

Attest:

BRUCE LEHMAN

*Attesting Officer*     *Commissioner of Patents and Trademarks*